US005486880A

United States Patent [19]
House

[11] Patent Number: 5,486,880
[45] Date of Patent: Jan. 23, 1996

[54] APPARATUS FOR CAUSING PUPIL CONSTRICTION

[76] Inventor: Paul M. House, 20 Boat La., Oswego, Ill. 60543

[21] Appl. No.: 252,369

[22] Filed: Jun. 1, 1994

[51] Int. Cl.⁶ .................................................. G02C 1/00
[52] U.S. Cl. ........................................... 351/158; 351/243
[58] Field of Search ..................................... 351/158, 243, 351/200, 203; 128/664, 665; 606/201, 204.25; 607/80

[56] References Cited

U.S. PATENT DOCUMENTS

| | | | |
|---|---|---|---|
| 2,741,245 | 4/1956 | Lange | 128/76.5 |
| 3,025,754 | 3/1962 | Mirsky | 88/20 |
| 3,074,397 | 1/1963 | Gernet | 128/76.5 |
| 3,507,552 | 4/1970 | Scott | 350/160 |
| 4,751,691 | 6/1988 | Perera | 368/10 |
| 5,092,669 | 3/1992 | Anderson | 351/158 |
| 5,102,409 | 4/1992 | Balgorod | 606/5 |
| 5,263,951 | 11/1994 | Spears et al. | 606/12 |

Primary Examiner—William L. Sikes
Assistant Examiner—Huy Mai
Attorney, Agent, or Firm—Marshall, O'Toole, Gerstein, Murray & Borun

[57] ABSTRACT

An apparatus for causing constriction of the pupils of a person's eyes which have corneal deformities so that light is not refracted through the corneal deformities, thus impairing the vision of the person. The apparatus includes a support frame with a first frame member having a nose rest associated therewith, a second frame member having an ear rest associated therewith, a first hinge which connects the second frame member to the first frame member, a third frame member having an ear rest associated therewith, and a second hinge which connects the third frame member to the first frame member. A first light source supported by the support frame generates light of an intensity sufficient to cause constriction of the pupil of one eye of the person, and a second light source supported by the support frame generates light of an intensity sufficient to cause constriction of the pupil of the other eye of the person.

35 Claims, 2 Drawing Sheets

APPARATUS FOR CAUSING PUPIL CONSTRICTION

BACKGROUND OF THE INVENTION

The present invention is directed towards an apparatus for causing constriction of the pupils of the eyes of a person, and more particularly to an apparatus for causing constriction of the pupils of the eyes of a person to prevent vision impairment resulting from deformities in the cornea which cause light entering the person's eyes to be improperly refracted by the cornea.

A cross-section of the human eye is illustrated in FIG. 1. The eye has a cornea 10 at the outermost front portion of the eye, an iris 12 which is annular in shape, and a lens 14 disposed adjacent the side of the iris 12 opposite the cornea 10. The iris 12 has a circular opening at its center which is referred to as the pupil 16. The iris 12 is composed of light-sensitive tissue, and its size changes in response to the intensity of light. As a result, the pupil 16 dilates in the presence of relatively weak light and constricts in the presence of relatively strong light. The retina 18 is disposed on the back surface of the eye. Visual images are generated by the eye by detecting light passing through the cornea 10, the pupil 12, and the lens 14 and converting light images falling on the retina 18 to optic signals, which are transmitted to the brain via the optic nerve 20.

A number of people have deformities in the corneas of their eyes which cause vision impairment, particularly at night. Such deformities include naturally occurring deformities, such as an irregular curvature of the cornea around its edges which occurs in the eyes of some myopic people, and artificially caused deformities, such as scar tissue resulting from eye surgery. One type of eye surgery that generates such deformities is a procedure referred to as radial keratotomy (RK). The RK procedure is performed in an attempt to correct the vision of a person to obviate the need to wear eyeglasses. In the RK procedure, a number of radial slits are made in the outer periphery of the cornea to change the curvature of the cornea, and therefore change the effective focal length of the eye.

An undesirable effect of the RK procedure is the formation of scar tissue where the radial slits in the cornea were made. Although the scar tissue does not interfere with vision during the day, it typically results in vision impairment at night, causing a "starburst" effect, which substantially impairs night vision and may cause night blindness.

The inventor realized that the vision impairment caused by the RK procedure generally occurs only at night because the pupils of a person's eyes are larger at night. FIG. 2A is a schematic representation, as it would appear during the daytime, of the eye of a person who has undergone the RK procedure. Referring to FIG. 2A, a plurality of radial deformities resulting from scar tissue are designated with the numeral 22. The deformities 22, which generally correspond in size to the radial slits that were performed during the RK procedure, do not extend sufficiently to reach the pupil 16, which is relatively small because of the generally strong light during the daytime. Because the deformities 22 do not extend over the pupil 16, any light that is improperly refracted by the cornea 10 due to the deformities 22 does not pass through the pupil 16 and therefore does not adversely affect vision.

However, when the pupil 16 dilates due to the relatively weak light generated at night, such as the light intensity that would be encountered while driving at night, the ends of the deformities 22 overlap the pupil 16 as shown in FIG. 2B. As a result, a portion of the light that is improperly refracted by the deformities 22 does pass through the pupil 16 to the retina 18, and thus interferes with the person's vision.

The vision impairment caused by deformities in the cornea has serious consequences, such as the inability to drive at night. Due to the irregular manner in which the corneal deformities affects vision, the vision impairment cannot be remedied by simply wearing corrective lenses. This condition may be treated to some extent by medication which restricts the normal dilation of the pupil. However, such medication has relatively long-term effects and would prevent a person's eyes from readily adapting to light conditions changing over a relatively short period of time.

SUMMARY OF THE INVENTION

The invention is directed to an apparatus for causing constriction of the pupils of a person's eyes to prevent vision impairment caused by improper refraction of light through deformities in the corneas of the person's eyes. The apparatus includes light-generating means for generating light of an intensity sufficient to cause constriction of the person's pupils to a degree sufficient to prevent light from being refracted through the deformities, and means for supporting the light-generating means in a fixed position with respect to the eyes of the person so that said light generated by the light-generating means is directed towards the pupils of the person and causes constriction of the pupils. Because the person's pupils are constricted, light does not pass through, and is not improperly refracted by, the deformities in the person's corneas. Consequently, the vision impairment caused by the deformities, which might prevent the person from driving at night for example, is prevented.

The intensity of the light generated towards the person's eyes to cause pupil constriction may range from a value of about 25 millicandles per eye to a value of about 200 millicandles per eye. Although light intensities higher than 200 millicandles per eye would cause pupil constriction, such intensities may be uncomfortable to the person and/or may unduly diminish the person's night vision, despite the fact that light would not pass through the deformities in the person's corneas.

The light-generating means may be provided in the form of a pair of light sources, each light source generating light of an intensity sufficient to cause constriction of the pupil of one of the person's eyes. Each of the pair of light sources may be directed to cause constriction of the pupil of a respective one of the person's eyes. Each light source may be composed of one or more light-generating devices, such as a light-emitting diode that generates a directional beam of light.

The means for supporting the light sources in a fixed relationship with respect to the person's eyes may comprise a conventional pair of eyeglass frames, with or without any corrective lenses provided therein. The support means may be provided with means for adjusting the intensity of the generated by the light sources, such as a rheostat, so that the person can adjust the light intensity to be bright enough to cause sufficient constriction of the person's pupils, but not too bright to be uncomfortable or to diminish the person's night vision by constricting the person's pupils to a greater degree than necessary.

These and other features and advantages of the present invention will be apparent to those of ordinary skill in the art in view of the detailed description of the preferred embodiment, which is made with reference to the drawings, a brief description of which is provided below.

DETAILED DESCRIPTION OF A PREFERRED EMBODIMENT

Figure 1:
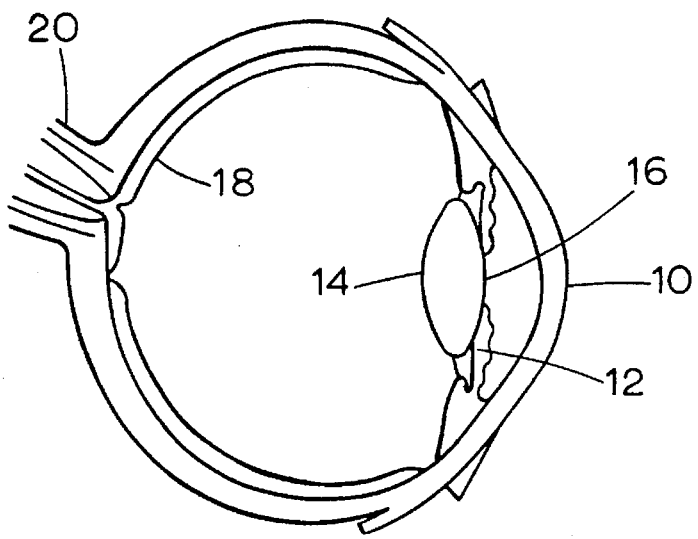
FIG. 1 is a cross-sectional view of the human eye.
Figure 2A:
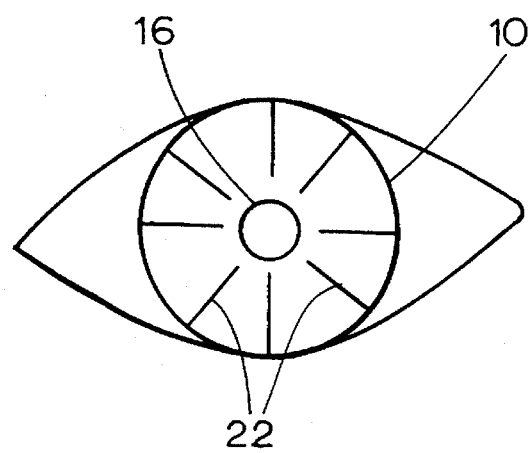
FIG. 2A is a schematic front view of a human eye having a plurality of radial deformities in the cornea and a pupil of relatively small size.
Figure 2B:
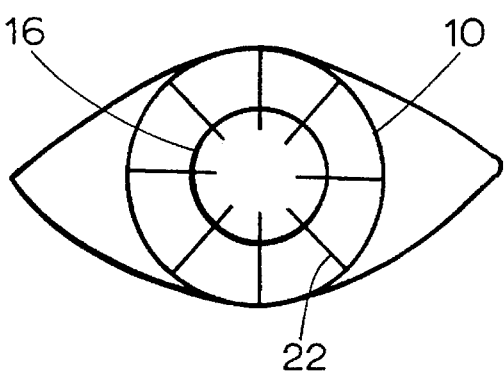
FIG. 2B is a schematic front view of the eye of FIG. 2A in which the pupil is of relatively large size.
Figure 3:
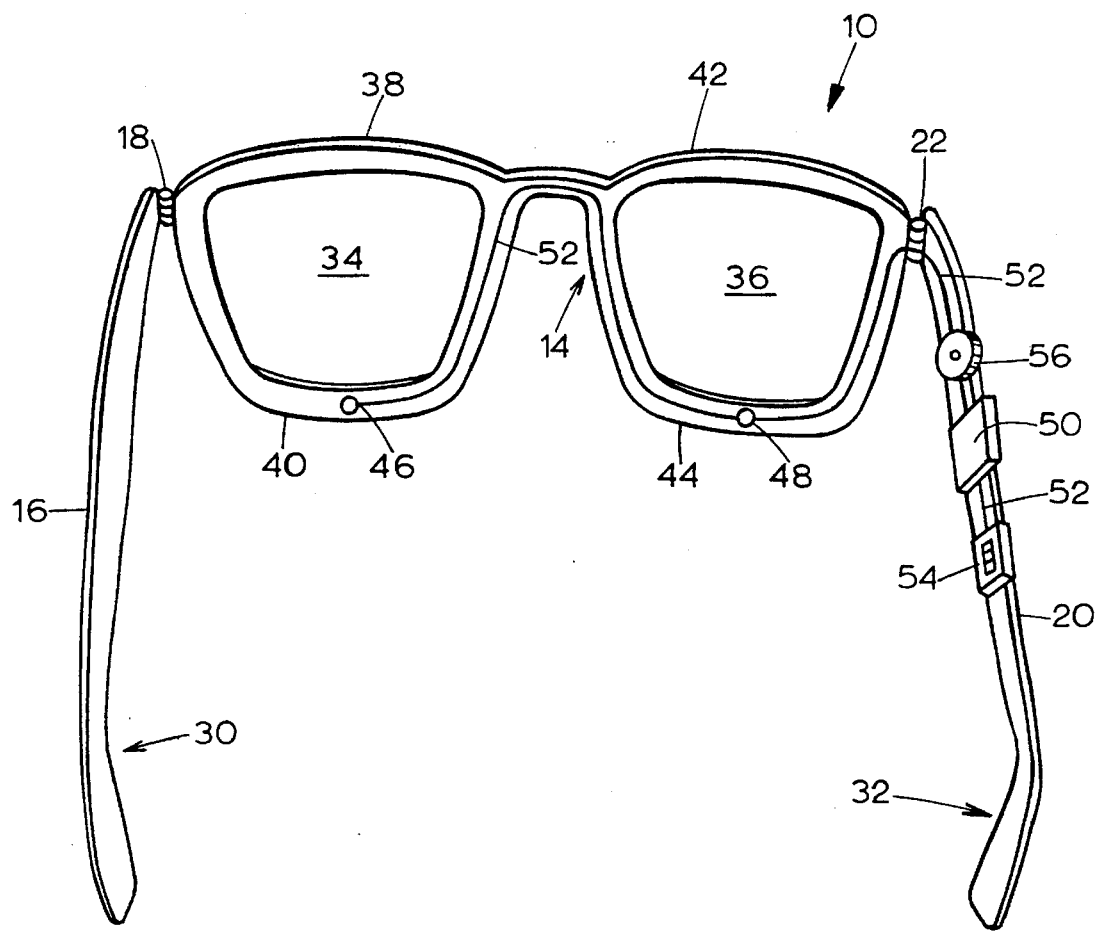
FIG. 3 illustrates one embodiment of the invention.

One embodiment of an apparatus 10 for causing pupil constriction in accordance with the invention is shown in FIG. 3. Referring to FIG. 3, the apparatus 10 has a support frame, similar to conventional eyeglass frames, which is composed of a frontal frame member 12 with a nose rest 14 formed therein, a first side frame member 16 pivotally connected to the frame member 12 via a hinge 18, and a second side frame member 20 pivotally connected to the frontal frame member 12 via a hinge 22. Each of the side frame members 16, 20 has one of a pair of ear rests 30, 32 associated therewith.

The frontal frame member 12 has a pair of openings in which a pair of lenses 34, 36 are disposed. The left-hand lens 34 is enclosed and supported by an upper frame portion 38 and a lower frame portion 40, and the right-hand lens 36 is enclosed and supported by an upper frame portion 42 and a lower frame portion 44. The lenses 34, 36 may be corrective lenses or flat lenses which provide no vision correction. The lenses 34, 36 may also be omitted from the apparatus 10.

A light-generating device or light source 46 is mounted on the lower frame portion 40 so that, when the apparatus 10 is worn by a person, the light source 46 emits light in a direction towards the pupil of the person's left eye. A light-generating device or light source 48 is mounted on the lower frame portion 44 so that, when the apparatus 10 is worn by a person, the light source 48 emits light in a direction towards the pupil of the person's right eye.

The light sources 46, 48 are connected to a source of power, such as a battery 50, via an electrical conductor or wire 52. The wire 52, which may constitute an electrically insulated twisted wire pair, may be provided in a groove or recess (not shown) formed in the sides of the frame support facing towards the person. The wire 52 electrically connects the light sources 46, 48 to an on/off switch 54, which may be switched by the person to turn off the light sources 46, 48 when the apparatus 10 is not in use.

Figure 4:
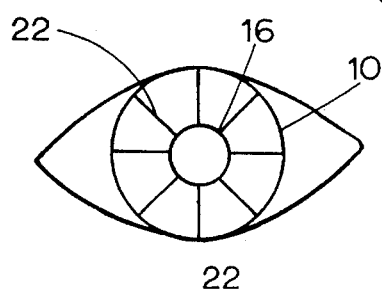
FIG. 4 is a schematic front view of a human eye having a plurality of radial deformities in the cornea and in which the pupil is constricted, by light generated by the embodiment of FIG. 3, to an optimum size.

The wire 52 may electrically connect the light sources 46, 48 to a means for adjusting the intensity of the light generated by the light sources 46, 48, such as a rheostat 56, so that the person wearing the apparatus 10 may adjust the intensity of the light so as to constrict the pupil just enough to prevent corneal deformities from adversely affecting the person's vision. For example, as illustrated in FIG. 4, the light generated by the light sources 46, 48 constricts the pupil 16 just enough so that it does not overlap the radial deformities 22.

Figure 5:
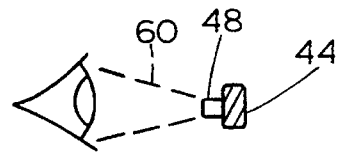
FIG. 5 is a schematic view of a light source that generates a directional beam of light directed towards the eye of a person.

Each of the light sources 46, 48 may comprise a light-emitting diode (LED) that, as illustrated in FIG. 5, generates a directional beam of light as indicated by dotted lines 60. One suitable LED, which is a 50-millicandle LED that generates yellow light, is marketed by Quality Technologies as Part Number MV5366. LEDs that generate light of a color other than yellow could also be used. Alternatively, each light source 46, 48 may comprise one or more small, incandescent or other light-generating devices.

The intensity of the light generated by the light sources 46, 48, as measured at each eye of the person, may range within a relatively broad range of between about 25 millicandles and about 200 millicandles, and within a narrower range of between about 50 millicandles and about 100 millicandles. Although light of an intensity greater than 200 millicandles would cause suitable constriction of the pupils of the person's eyes, such relatively intense light may adversely interfere with the person's vision. The intensity of the light most desirable depends upon the particular person wearing the apparatus 10. While light of an intensity of 50 millicandles has been found suitable for the inventor, other persons may require other intensities due to the different characteristics of their eyes and of any corneal deformities.

Modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. An apparatus for causing constriction of the pupil of an eye of a person having a deformity in the cornea of said eye so that light is not refracted through said deformity, impairing the vision of the person, said apparatus comprising:

light-generating means for generating light of an intensity sufficient to cause constriction of said pupil of the person to a degree sufficient to prevent light from being refracted through said deformity and thus to prevent impairment of the vision of the person; and support means for supporting said light-generating means in a fixed position with respect to said eye of the person so that said light generated by said light-generating means is directed towards said pupil of the person and causes constriction of said pupil without substantially obstructing the vision of the person.

2. An apparatus as defined in claim 1 wherein said support means comprises:

a support frame including:
   a first frame member having a nose rest associated therewith;
   a second frame member having an ear rest associated therewith;
   a first hinge which connects said second frame member to said first frame member;
   a third frame member having an ear rest associated therewith; and
   a second hinge which connects said third frame member to said first frame member.

3. An apparatus as defined in claim 1 wherein said light-generating means automatically generates said light continuously.

4. An apparatus as defined in claim 1 wherein said intensity of said light at said eye is at least about 25 millicandles.

5. An apparatus as defined in claim 1 wherein said intensity of said light at said eye is at least about 50 millicandles.

6. An apparatus as defined in claim 1 wherein said intensity of said light at said eye is between about 25 millicandles and about 200 millicandles.

7. An apparatus as defined in claim 1 wherein said intensity of said light at said eye is between about 50 millicandles and about 100 millicandles.

8. An apparatus as defined in claim 1 wherein said light-generating means comprises means for generating a directional beam of light, said beam being directed at said eye.

9. An apparatus as defined in claim 1 additionally comprising means for adjusting said intensity of said light.

10. An apparatus as defined in claim 1 additionally comprising a rheostat, electrically connected to said light-generating means, for adjusting said intensity of said light.

11. An apparatus as defined in claim 1,
wherein said apparatus causes constriction of the pupils of both eyes of the person,
wherein said light-generating means comprises a first light source that generates light of an intensity sufficient to cause constriction of the pupil of an eye of the person and a second light source that generates light of an intensity sufficient to cause constriction of the pupil of an eye of the person, and
wherein said support means comprises means for supporting said first and second light sources so that said light emitted from said first light source is directed towards one eye of the person and so that said light emitted from said second light source is directed towards the other eye of the person.

12. An apparatus as defined in claim 11 wherein said intensity of said light at each eye of the person is at least about 25 millicandles.

13. An apparatus as defined in claim 11 wherein said intensity of said light at each eye of the person is at least about 50 millicandles.

14. An apparatus as defined in claim 11 wherein said intensity of said light at each eye of the person is between about 25 millicandles and about 200 millicandles.

15. An apparatus as defined in claim 11 wherein said intensity of said light at each eye of the person is between about 50 millicandles and about 100 millicandles.

16. An apparatus for causing constriction of the pupils of the eyes of a person, said apparatus comprising:
a support frame including:
a first frame member having a nose rest associated therewith and a lens disposed therein;
a second frame member having an ear rest associated therewith;
a first hinge which connects said second frame member to said first frame member;
a third frame member having an ear rest associated therewith; and
a second hinge which connects said third frame member to said first frame member;
a first light source supported by said support frame, said first light source generating light of an intensity sufficient to cause constriction of a first pupil of the person, said first light source supported by said support frame in a direction to cause said light from said first light source to be directed towards said first pupil so that said first pupil is constricted by said light from said first light source; and
a second light source supported by said support frame, said second light source generating light of an intensity sufficient to cause constriction of a second pupil of the person, said second light source supported by said support frame in a direction to cause said light from said second light source to be directed towards said second pupil so that said second pupil is constricted by said light from said second light source.

17. An apparatus as defined in claim 16 wherein said first and second light sources automatically generate said light continuously.

18. An apparatus as defined in claim 16 wherein said intensity of said light at each eye of the person is at least about 25 millicandles.

19. An apparatus as defined in claim 16 wherein said intensity of said light at each eye of the person is at least about 50 millicandles.

20. An apparatus as defined in claim 16 wherein said intensity of said light at each eye of the person is between about 25 millicandles and about 200 millicandles.

21. An apparatus as defined in claim 16 wherein said intensity of said light at each eye of the person is between about 50 millicandles and about 100 millicandles.

22. An apparatus as defined in claim 16 additionally comprising means for adjusting said intensity of said light.

23. An apparatus as defined in claim 16 additionally comprises a rheostat, electrically connected to said first and second light sources, for adjusting said intensity of said light.

24. An apparatus as defined in claim 16 wherein said first light source comprises means for generating a first directional beam of light, said first directional beam being directed at said first pupil.

25. An apparatus as defined in claim 24 wherein said second light source comprises means for generating a second directional beam of light, said second directional beam being directed at said second pupil.

26. An apparatus for causing constriction of the pupils of the eyes of a person, said apparatus comprising:
a support structure which may be disposed in a fixed position with respect to the eyes of the person;
a first light source that generates light of an intensity sufficient to cause constriction of the pupil of a first eye of the person; and
a second light source that generates light of an intensity sufficient to cause constriction of the pupil of a second eye of the person,
said support structure having means for supporting said first and second light sources in a fixed position with respect to said eyes of the person so that said light generated by each of said light sources is directed towards a respective one of said pupils of the person and causes constriction of one of said pupils without substantially obstructing the vision of the person.

27. An apparatus as defined in claim 26 wherein said support structure comprises:
a first frame member having a nose rest associated therewith;
a second frame member having an ear rest associated therewith;
a first hinge which connects said second frame member to said first frame member;
a third frame member having an ear rest associated therewith; and a second hinge which connects said third frame member to said first frame member.

28. An apparatus as defined in claim 26 wherein each of said first and second light sources comprises means for automatically generating said light continuously.

29. An apparatus as defined in claim 26 wherein said intensity of said light is at least about 25 millicandles.

30. An apparatus as defined in claim 26 wherein said intensity of said light is at least about 50 millicandles.

31. An apparatus as defined in claim 26 wherein said intensity of said light is between about 25 millicandles and about 200 millicandles.

32. An apparatus as defined in claim 26 wherein said intensity of said light is between about 50 millicandles and about 100 millicandles.

33. An apparatus as defined in claim 26 additionally comprising means for adjusting said intensity of said light.

34. An apparatus as defined in claim 26 additionally comprising a rheostat, electrically connected to said light-generating means, for adjusting said intensity of said light.

35. An apparatus as defined in claim 26 wherein said first light source comprises means for generating a first directional beam of light, said first directional beam being directed at said first eye, and wherein said second light source comprises means for generating a second directional beam of light, said second directional beam being directed at said second eye.

* * * * *